United States Patent
Andon et al.

(10) Patent No.: US 11,350,692 B2
(45) Date of Patent: Jun. 7, 2022

(54) AUTOLACING FOOTWEAR SYSTEM WITH PRESET USER PROFILES

(71) Applicant: NIKE, Inc., Beaverton, OR (US)

(72) Inventors: Christopher Andon, Portland, OR (US); Yujin Lee, Portland, OR (US); Kiran Kripakaran, Portland, OR (US); Bryan Martz, Portland, OR (US)

(73) Assignee: NIKE, Inc., Beaverton, OR (US)

(*) Notice: Subject to any disclaimer, the term of this patent is extended or adjusted under 35 U.S.C. 154(b) by 691 days.

(21) Appl. No.: 16/171,265

(22) Filed: Oct. 25, 2018

(65) Prior Publication Data

US 2019/0116915 A1 Apr. 25, 2019

Related U.S. Application Data

(60) Provisional application No. 62/576,691, filed on Oct. 25, 2017.

(51) Int. Cl.
*A43B 3/34* (2022.01)
*A43C 1/00* (2006.01)
(Continued)

(52) U.S. Cl.
CPC .................. *A43B 3/34* (2022.01); *A43C 1/00* (2013.01); *A43C 1/04* (2013.01); *A43C 7/005* (2013.01);
(Continued)

(58) Field of Classification Search
CPC .......... A43B 3/0005; A43C 19/00; G06F 3/01
(Continued)

(56) References Cited

U.S. PATENT DOCUMENTS 9,606,647 B1* 3/2017 Spencer-Harper .... G06F 3/0482
9,730,494 B1   8/2017 Feinstein
(Continued)

FOREIGN PATENT DOCUMENTS

CN       1839724     10/2006
CN     101454812      6/2009
(Continued)

OTHER PUBLICATIONS

English translation of JP 2021500961, Jan. 2021. (Year: 2021).*
(Continued)

*Primary Examiner* — Michael P Nghiem
(74) *Attorney, Agent, or Firm* — Schwegman Lundberg & Woessner, P.A.

(57) ABSTRACT

A system includes an article of footwear and a remote system. The article of footwear includes an adaptive configured to be adjusted to one of a plurality of configurations based on a command received from a processor circuit. The remote system includes an electronic data storage, configured to store a user profile including the plurality of configurations, and a processor configured to prompt, on a user interface, a user to put on the article of footwear, receive, via a wireless transceiver, a signal from the article of footwear indicating that the article of footwear has been placed on the foot of a wearer, access, one of the plurality of configurations based on a user selection, and transmit the one of the plurality of configurations as selected. The processor circuit causes the adaptive component to be configured according to the one of the plurality of configurations.

28 Claims, 13 Drawing Sheets

(51) Int. Cl.
  *A43C 7/00* (2006.01)
  *A43C 19/00* (2006.01)
  *A43C 1/04* (2006.01)
  *G06F 3/0482* (2013.01)
  *A43C 11/00* (2006.01)
  *A61F 5/14* (2022.01)

(52) U.S. Cl.
  CPC ............ *A43C 11/008* (2013.01); *A43C 19/00* (2013.01); *A61F 5/14* (2013.01); *G06F 3/0482* (2013.01)

(58) Field of Classification Search
  USPC .......................................................... 702/85
  See application file for complete search history.

(56) References Cited

U.S. PATENT DOCUMENTS

| | | |
|---|---|---|
| 2005/0183292 A1 | 8/2005 | Dibenedetto et al. |
| 2009/0284368 A1* | 11/2009 | Case, Jr. .............. A43B 3/0005 340/539.1 |
| 2011/0239488 A1 | 10/2011 | Carnes et al. |
| 2011/0260857 A1 | 10/2011 | Hamill |
| 2014/0070042 A1* | 3/2014 | Beers ................... A43B 3/0015 242/413 |
| 2015/0048942 A1 | 2/2015 | Bertagna et al. |
| 2016/0113355 A1 | 4/2016 | Bliss |
| 2017/0099913 A1 | 4/2017 | Beers et al. |
| 2017/0265582 A1* | 9/2017 | Walker ................... A43B 3/001 |
| 2017/0272008 A1 | 9/2017 | Schneider |

FOREIGN PATENT DOCUMENTS

| | | |
|---|---|---|
| CN | 107242633 | 10/2017 |
| CN | 111278320 | 6/2020 |
| CN | 113397265 | 9/2021 |
| JP | 2008054890 | 3/2008 |
| JP | 2013132326 | 7/2013 |
| JP | 2021500961 A | 1/2021 |
| JP | 2022008544 | 1/2022 |
| KR | 1020200062359 | 6/2020 |
| KR | 102188633 B1 | 12/2020 |
| KR | 20200139269 A | 12/2020 |
| KR | 1020210100220 | 8/2021 |
| WO | 2014036371 | 3/2014 |
| WO | 2017092775 | 6/2017 |
| WO | 2019084333 | 5/2019 |
| WO | WO-2019084333 A2 | 5/2019 |
| WO | 2019084333 | 7/2019 |
| WO | WO-2019084333 A3 | 7/2019 |

OTHER PUBLICATIONS

English translation of KR 102188633, Dec. 2020. (Year: 2020).*
English translation of KR 20200139269. Dec. 2020. (Year: 2020).*
English translation of Chinese Response filed Mar. 16, 2021 to Office Action dated Nov. 17, 2020. (Year: 2021).*
English translation of JP Decision of Final Refusal dated May 25, 2021. (Year: 2021).*
English translation of JP Response filed Feb. 22, 2021 to Refusal dated Nov. 24, 2020. (Year: 2021).*
English translation of Response filed Sep. 24, 2021 to Examiner's Decision of Final Refusal dated May 25, 2021. (Year: 2021).*
"Japanese Application Serial No. 2020-523443, Notification of Reasons for Refusal dated Nov. 24, 2020", w Concise Statement of Relevance, 5 pgs.
"Chinese Application Serial No. 201880069599.0, Office Action dated Nov. 17, 2020", w Concise Statement of Relevance, 6 pgs.
"International Application Serial No. PCT US2018 057603, International Search Report dated Jun. 4, 2019", 4 pgs.
"International Application Serial No. PCT US2018 057603, Written Opinion dated Jun. 4, 2019", 6 pgs.
"International Application Serial No. PCT US2018 057603, International Preliminary Report on Patentability dated May 7, 2020", 8 pgs.
"European Application Serial No. 18871226.9, Extended European Search Report dated Sep. 21, 2020", 10 pgs.
"European Application Serial No. 18871226.9, Response filed Apr. 1, 2021 to Extended European Search Report dated Sep. 21, 2020", 35 pgs.
"Japanese Application Serial No. 2020-523443, Response filed Sep. 24, 2021 to Examiners Decision of Final Refusal dated May 25, 2021", With English claims, 12 pgs.
"Korean Application Serial No. 10-2021-7024910, Notice of Preliminary Rejection dated Dec. 21, 2021", w English translation, 7 pgs.
"Chinese Application Serial No. 202110660955.X, Voluntary Amendment filed Jan. 10, 2022", With English claims, 81 pgs.
"Chinese Application Serial No. 202110660955.X, Office Action dated Mar. 17, 2022", With English machine translation, 28 pgs.

* cited by examiner

AUTOLACING FOOTWEAR SYSTEM WITH PRESET USER PROFILES

PRIORITY

This application claims the benefit of priority to U.S. Provisional Application No. 62/576,691, titled MOTORIZED TENSIONING SYSTEM SITH SENSORS, filed Oct. 25, 2017, which is incorporated by reference herein in its entirety.

TECHNICAL FIELD

The subject matter disclosed herein generally relates to an article of footwear having an autolacing system or other adaptive component and a related system with preset user profiles.

BRIEF DESCRIPTION OF THE DRAWINGS

Some embodiments are illustrated by way of example and not limitation in the figures of the accompanying drawings.

DETAILED DESCRIPTION

Figure 1:
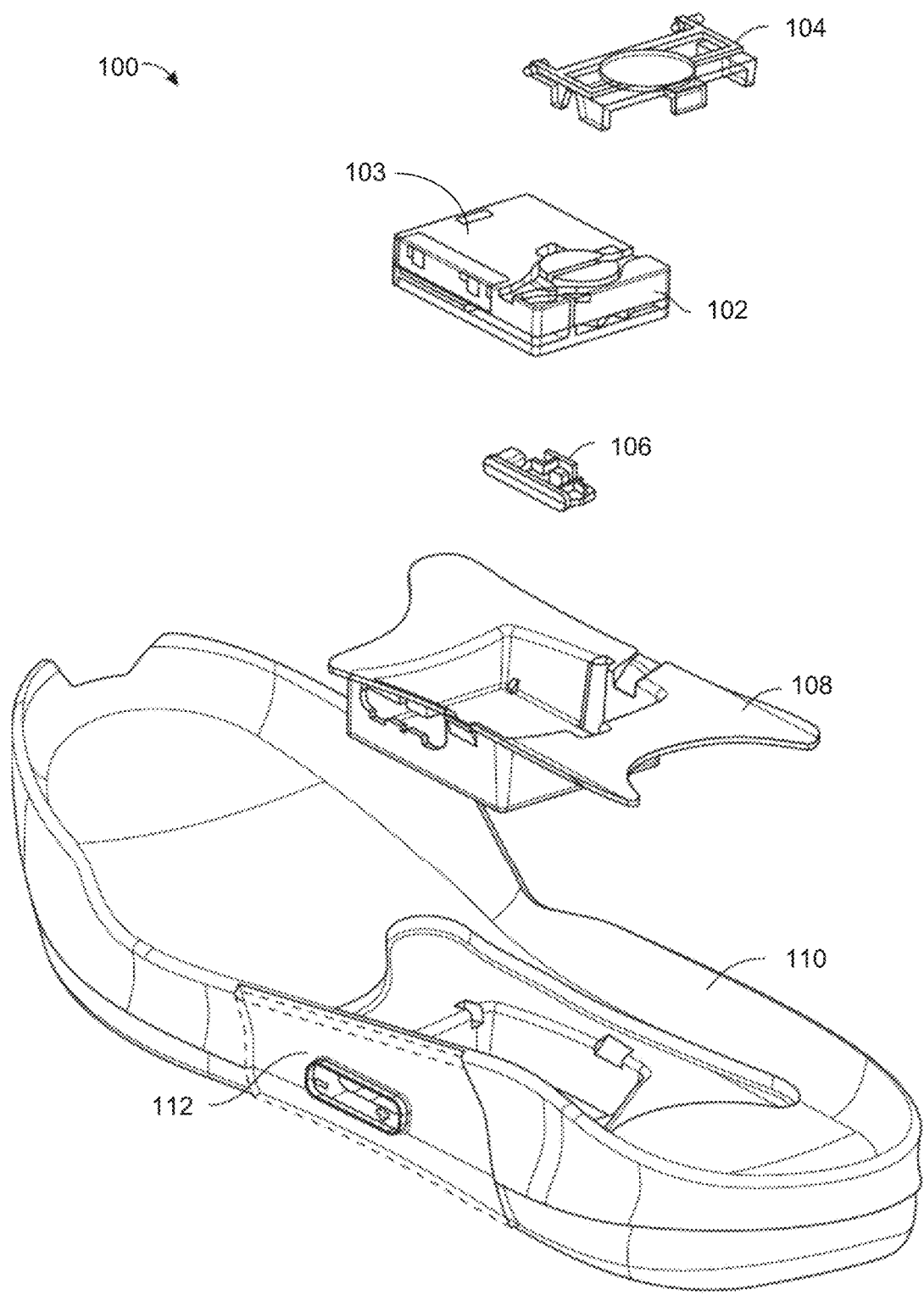
FIG. 1 is an exploded view illustration of components of a motorized lacing system for an article of footwear, in an example embodiment.

Example methods and systems are directed to an article of footwear having an autolacing system or other adaptive component and a related system with preset user profiles. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

Articles of footwear, such as shoes, may include a variety of components, both conventional and unconventional. Conventional components may include an upper, a sole, and laces or other securing mechanisms to enclose and secure the foot of a wearer within the article of footwear. Unconventionally, an adaptive component or components, such as a motorized lacing system may engage with the lace to tighten and/or loosen the lace. Additional or alternative adaptive components may electrically or mechanically change or adapt various additional aspects of the article of footwear to the wearer or to the circumstances in which the wearer is using the article of footwear. For instance, the adaptive component may change a cushioning system to be firm or soft or adapt the cushioning system to the compensate for a turn or "cut" during a game. The motorized lacing system or adaptive component in general may be controlled by a controller and other electronics, including operating and driving the motor, sensing information about the nature of the article of footwear, providing lighted displays and/or other sensory stimuli, and so forth.

How adaptive components in footwear are utilized may be dependent on the characteristics and preferences of the wearer and the circumstances in which the wearer is wearing the footwear. A wearer may have a relatively wide or narrow foot for their size. A wearer may, over the course of their use of the footwear, wear the footwear casually, for running, or for basketball, and may benefit from different configurations of the adaptive component in different activities. A wearer may simply prefer the footwear to be relatively tight or relatively loose in comparison to other wearers.

Moreover, a user may purchase multiple different pairs of footwear having adaptive components. For instance, a user may have multiple pairs of autolacing footwear simultaneously or consecutively. The user's preferences for auotlacing footwear may be consistent, but the nature of the different pairs of footwear may be different. For instance, one pair of footwear may be geared toward running, and thus may provide structure and cushioning optimized for moving straight forward and gentle turns, while a second pair may be geared toward basketball, and thus may provide structure and cushioning optimized for short sprints and sudden stops and turns. As such, the precise settings for the adaptive component on one article of footwear may not be directly applicable to the other article of footwear.

A system has been developed that provides a user of an article of footwear with an adaptive component with a user profile that automatically baselines a maximum configuration of a certain feature, such as lace tension in autolacing applications, and establishing multiple configurations for the user. The maximum feature and the multiple configurations are transferrable and portable across multiple articles of footwear that include the same type of adaptive component, but which are applied to the detailed configuration of the specific article of footwear. Thus, for instance, configurations for one article of footwear may be translated to provide a similar feel in a different article of footwear. A user interface may provide for a user to adjust and set the configurations and the user profile more generally. Wireless communications may permit remote users to adjust a configuration remotely while the footwear is being worn without requiring input from the wearer.

FIG. 1 is an exploded view illustration of components of a motorized lacing system for an article of footwear, in an example embodiment. While the system is described with respect to the article of footwear, it is to be recognized and understood that the principles described with respect to the article of footwear apply equally well to any of a variety of wearable articles. The motorized lacing system 100 illustrated in FIG. 1 includes a lacing engine 102 having a housing structure 103, a lid 104, an actuator 106, a mid-sole plate 108, a mid-sole 110, and an outsole 112. FIG. 1 illustrates the basic assembly sequence of components of an automated lacing footwear platform. The motorized lacing system 100 starts with the mid-sole plate 108 being secured within the mid-sole. Next, the actuator 106 is inserted into an opening in the lateral side of the mid-sole plate opposite to interface buttons that can be embedded in the outsole 112. Next, the lacing engine 102 is dropped into the mid-sole plate 108. In an example, the lacing system 100 is inserted under a continuous loop of lacing cable and the lacing cable is aligned with a spool in the lacing engine 102 (discussed below). Finally, the lid 104 is inserted into grooves in the mid-sole plate 108, secured into a closed position, and latched into a recess in the mid-sole plate 108. The lid 104 can capture the lacing engine 102 and can assist in maintaining alignment of a lacing cable during operation.

Figure 2:
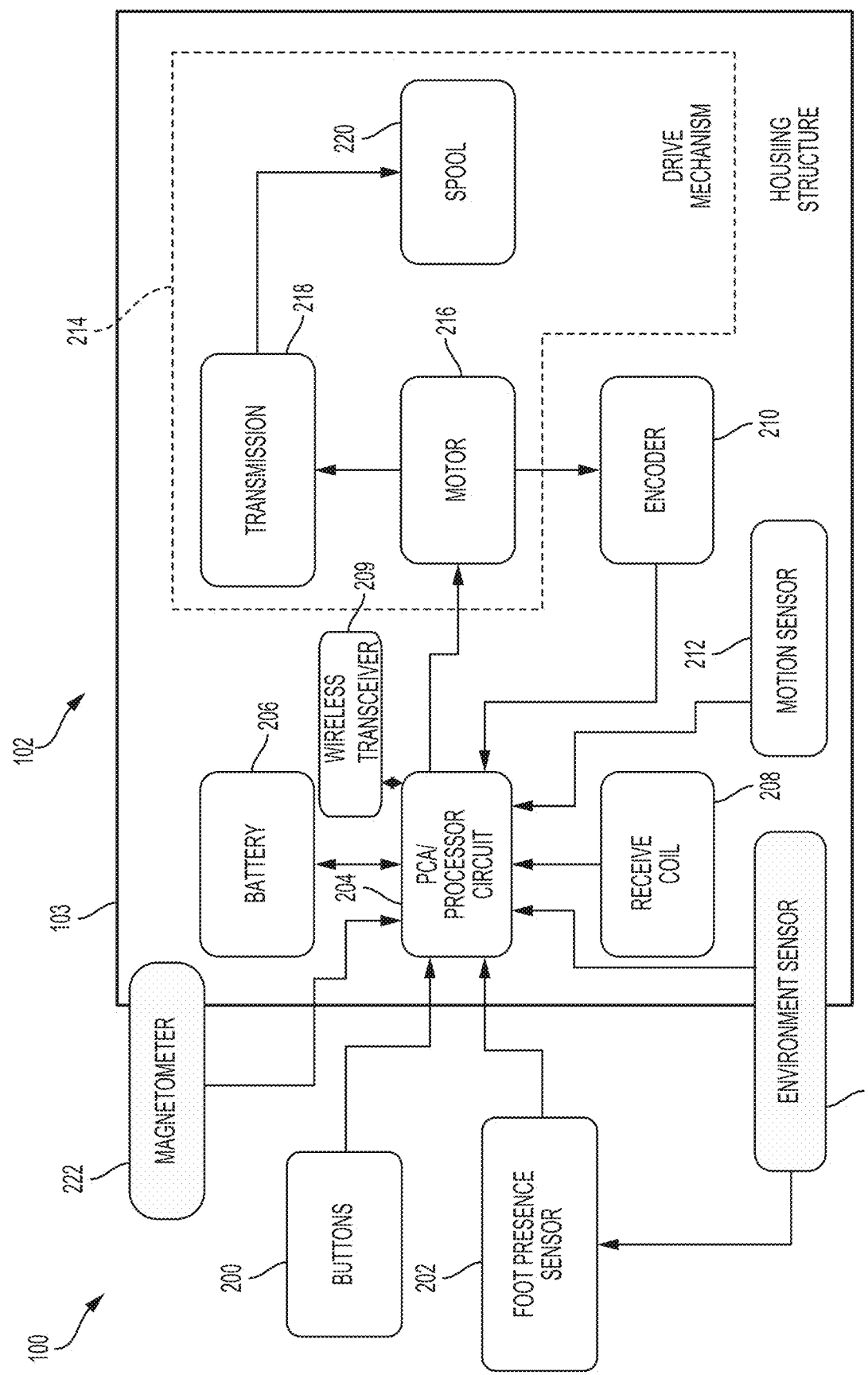
FIG. 2 illustrates generally a block diagram of components of a motorized lacing system, in an example embodiment.

FIG. 2 illustrates generally a block diagram of components of a motorized lacing system 100, in an example embodiment. The system 100 includes some, but not necessarily all, components of a motorized lacing system such as including interface buttons 200, a foot presence sensor 202, and the lacing engine housing 102 enclosing a printed circuit board assembly (PCA) with a processor circuit 204, a battery 206, a receive coil 208 a wireless transceiver 209, including a wireless transmitter and a wireless receiver, an optical encoder 210, a motion sensor 212, and a drive mechanism 214. The optical encoder 210 may include an optical sensor and an encoder having distinct portions independently detectable by the optical sensor. The drive mechanism 214 can include, among other things, a motor 216, a transmission 218, and a lace spool 220, The motion sensor 212 can include, among other things, a single or multiple axis accelerometer, a magnetometer, a gyrometer, or other sensor or device configured to sense motion of the housing structure 102, or of one or more components within or coupled to the housing structure 102. In an example, the motorized lacing system 100 includes a magnetometer 222 coupled to the processor circuit 204.

FIG. 2 illustrates generally a block diagram of components of a motorized lacing system 100, in an example embodiment. The system 100 includes some, but not necessarily all, components of a motorized lacing engine 102 including interface buttons 200, a foot presence sensor 202, and the lacing engine housing 103 enclosing a printed circuit board assembly (PCA) with a processor circuit 204, a battery 206, a receive coil 208 which may operate as part of a wireless transceiver, including a wireless transmitter and a wireless receiver, an optical encoder 210, a motion sensor 212, and a drive mechanism 214. The optical encoder 210 may include an optical sensor and an encoder having distinct portions independently detectable by the optical sensor. The drive mechanism 214 can include, among other things, a motor 216, a transmission 218, and a lace spool 220. The motion sensor 212 can include, among other things, a single or multiple axis accelerometer, a magnetometer, a gyrometer, or other sensor or device configured to sense motion of the housing structure 103, or of one or more components within or coupled to the housing structure 103. In an example, the motorized lacing system 100 includes a magnetometer 222 coupled to the processor circuit 204.

In the example of FIG. 2, the processor circuit 204 is in data or power signal communication with one or more of the interface buttons 200, foot presence sensor 202, battery 206, receive coil 208, and drive mechanism 214. The transmission 218 couples the motor 216 to a spool to form the drive mechanism 214. In the example of FIG. 2, the buttons 200, foot presence sensor 202, and environment sensor 224 are shown outside of, or partially outside of, the lacing engine 102.

In an example, the receive coil 208 is positioned on or inside of the housing 103 of the lacing engine 102. In various examples, the receive coil 208 is positioned on an outside major surface, e.g., a top or bottom surface, of the housing 103 and, in a specific example, the bottom surface. In various examples, the receive coil 208 is a qi charging coil, though any suitable coil, such as an A4WP charging coil, may be utilized instead.

In an example, the processor circuit 204 controls one or more aspects of the drive mechanism 214. For example, the processor circuit 204 can be configured to receive information from the buttons 200 and/or from the foot presence sensor 202 and/or from the motion sensor 212 and, in response, control the drive mechanism 214, such as to tighten or loosen footwear about a foot. In an example, the processor circuit 204 is additionally or alternatively configured to issue commands to obtain or record sensor information, from the foot presence sensor 202 or other sensor, among other functions. In an example, the processor circuit 204 conditions operation of the drive mechanism 214 on (1) detecting a foot presence using the foot presence sensor 202 and (2) detecting a specified gesture using the motion sensor 212.

Information from the environment sensor 224 can be used to update or adjust a baseline or reference value for the foot presence sensor 202. As further explained below, capacitance values measured by a capacitive foot presence sensor can vary over time, such as in response to ambient conditions near the sensor. Using information from the environment sensor 224, the processor circuit 204 and/or the foot presence sensor 202 can update or adjust a measured or sensed capacitance value.

Figure 3:
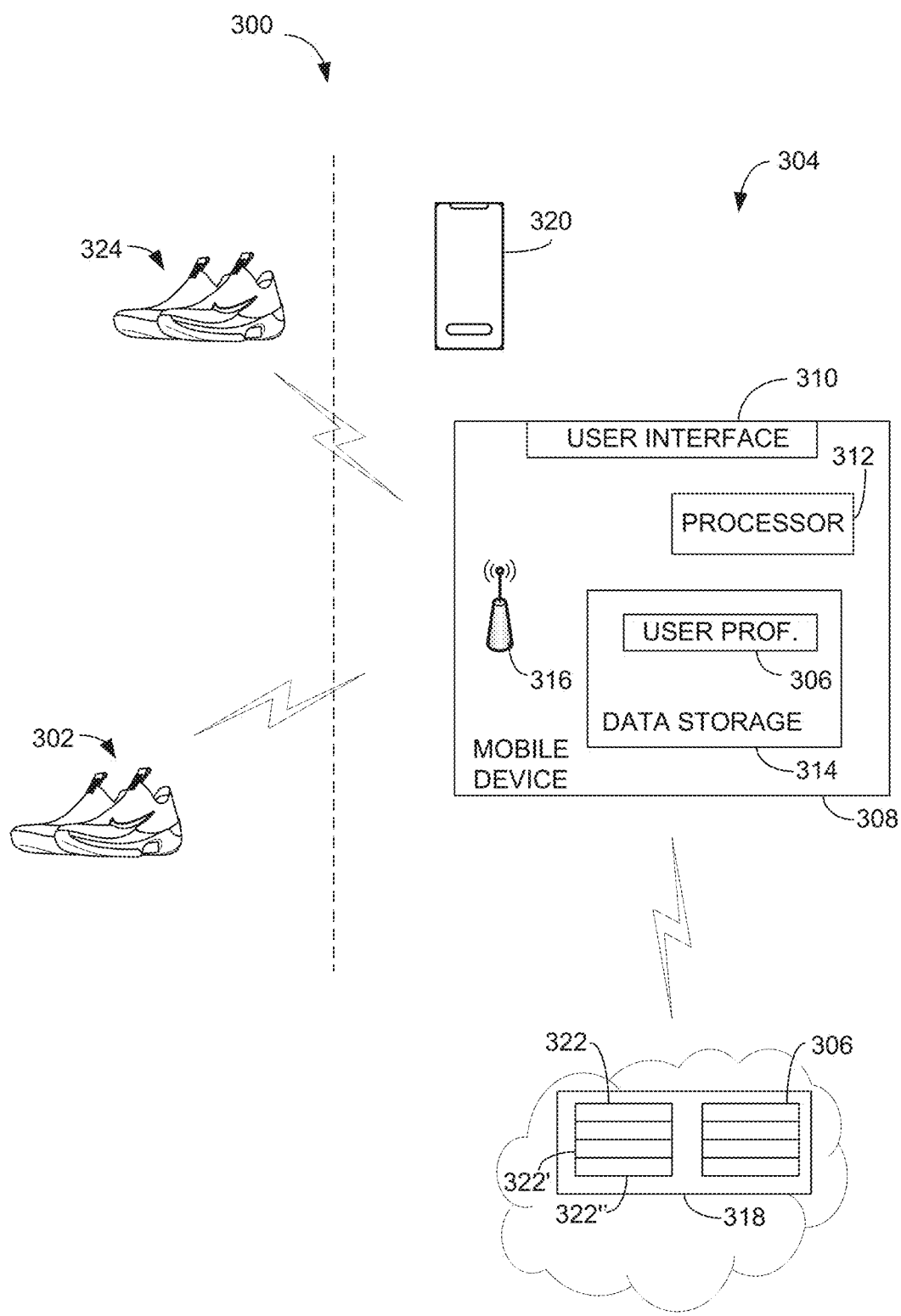
FIG. 3 is a system diagram including an article of footwear having the motorized lacing system and a remote electronic system that allows for a user profile to be created and manipulated, in an example embodiment.

FIG. 3 is a system diagram 300 including an article of footwear 302 (understood, for the purposes of this disclosure, to be either one article of a matched pair of articles of footwear) having the motorized lacing system 100 and a remote electronic system 304 that allows for a user profile 306 to be created and manipulated, in an example embodiment. While the system 300 is described with respect to the motorized lacing system 100, it is to be recognized and understood that the system 300 may be implemented with an article of footwear including any adaptive component, such as the adaptive support member with rheological fluid disclosed in U.S. Pat. No. 9,198,478, "Support Members With Variable Viscosity Fluid for Footwear", filed Mar. 5, 2013, which is incorporated by reference herein in its entirety. The system 300 includes multiple electronic components which may be incorporated into a single electronic device, such as a mobile device (e.g., a smartphone, tablet computer, smart watch, etc.), or may be a distributed system, including remote components accessed via a network and/or a smart watch operating in conjunction with a smartphone.

In the illustrated example, the remote electronic system 304 includes a mobile device 308, such as a smartphone, which includes a user interface 310, a processor 312, an electronic data storage 314 which may operate as a computer readable medium, and a wireless transceiver 316 which includes a wireless transmitter and a wireless receiver. The user interface 310 may include a visual display and a data entry device, such as a touchscreen, keyboard, audio recorder and translator, and the like, and an audio output, such as a speaker, headphone, or the like. The wireless transceiver 316 is configured to communicate with the wireless transceiver of the motorized lacing system 100 according to any of a variety of suitable wireless modalities, including Bluetooth, WiFI, and the like.

The user profile 306 is stored to the electronic data storage 314. The user profile 306 may be accessed by the processor 312 and information related to the user profile 306 displayed or otherwise presented to a user via the user interface 310. The user may adjust or apply the user profile 306 to adjust or otherwise control the motorized lacing system 100. As will be illustrated herein, the user may start an application or "app" related to controlling the motorized lacing system 100, select or login to their user profile or another user profile to which they have access, select between and among predetermined configurations, adjust the predetermined configurations, and manually adjust the motorized lacing system 100 without respect to one of the predetermined configurations.

The remote electronic system 304 may further include or may access additional systems via a network, e.g., via the wireless transceiver 316 communicating with WiFi, cellular, Bluetooth, or any suitable wireless technology. The additional systems may include a remote electronic data storage 318 which may include a database 320 which may store the user profile 306 along with other user profiles of other users. Upon the user logging in to the app via the user interface 310, the processor 312 may optionally download the user profile 306 from the remote electronic data storage 318 if the user profile 306 is not already stored on the local electronic data storage 314. Or, if the user profile 306 is already stored on the local electronic data storage 314, the processor 312 may check the user profile 306 as stored on the remote electronic data storage 318 to see if the user profile 306 has been updated on a different device and, if so, download the user profile 306 as updated and store the updated user profile 306 on the local electronic data storage 314. If the user updates the user profile 306 via the app the processor 312 may cause the user profile 306 as updated to be transmitted to the remote electronic data storage 318.

The system 300 may provide for control of the motorized lacing system 100 from authorized secondary devices 320, For instance, an authorized secondary device 320 may be a mobile device or computer controlled by a coach or manager of the user who is wearing the article of footwear 302 during a game, practice, or other team activity. The coach may utilized the authorized secondary device 320 to wirelessly reconfigure the motorized lacing system 100 without input from the user, e.g., during a game or practice if the wearer is not able to adjust the motorized lacing system 100 on their own. For instance, if a basketball player has a first configuration for the motorized lacing system 100 but over the course of playing in a basketball game the coach concludes the motorized lacing system 100 is not optimized for the actual playing conditions, the coach may utilize the app to access the user profile 306 on the authorized secondary device 320 and adjust the parameters of the motorized lacing system 100, e.g., by selecting a different preset configuration or manually adjusting tightness on the lace. The app may be utilized to adjust any of a variety of parameters of the articles of footwear 302, e.g., change lighting that is visible from the buttons 200, etc., for any and all articles of footwear that accessible via the authorized secondary device 320.

It is to be recognized that the remote control of the motorized lacing system 100 by the authorized secondary device 320 may be local to the article of footwear 302, e.g., by someone actually at the activity in which the user is wearing the article of footwear 302, or remotely via a network connection. Thus, an authorized user would not necessarily need to be present in order to adjust the motorized lacing system 100. Moreover, the purpose of the access to the motorized lacing system 100 or to an adaptive component more generally may be for a secondary reason. Thus, for instance, a coach may manipulate an adaptive component in order to send messages or feedback to the wearer.

Further, while the authorized user is described as a person, the authorized user may be an electronic system that operates automatically to adjust and adapt the performance of the motorized lacing system 100 or adaptive component more generally and/or send messages or otherwise communicate information to the wearer. Thus, for instance, if the electronic system determines that the settings on the motorized lacing system 100 are not optimal to the circumstances for whatever reason then the electronic system may adjust the parameters of the motorized lacing system 100. Further, if the electronic system determines that the wearer has moved out of a designated area on a playing field the electronic system may send a signal, e.g., by vibrating the motorized lacing system 100 in one of the articles of footwear 302, to signal to the wearer to adjust their position. See, e.g., PCT application publication number WO 2017/095956, "Shin Guard With Remote Haptic Feedback", filed. Nov. 30, 2016, claiming the benefit of priority to U.S. Provisional Application No. 62/261,149, both of which are incorporated herein by reference in their entirety.

The system 300 may include footwear profiles 322 describing properties of different types of articles of footwear that include the motorized lacing system 100 or different implementations of motorized lacing systems. Thus, for instance, the article of footwear 302 may have a footwear profile 322' that describes how the motorized lacing system 100 sets tension on the lace, e.g., positions of the lace spool 220, and physical properties of the article of footwear 302 generally. For instance, the footwear profile 322' may include dimensions of the article of footwear 302, properties of the materials of the article of footwear 302, e.g., the elasticity of components of the upper, and the layout of the lacing system of the article of footwear 302 and the locations of where tension is transferred from the lace onto the upper.

The system 300 may further incorporate a second article of footwear 324, understood for these purposes to be one or a matched pair of articles of footwear different than the article of footwear 302. The second article of footwear 324 may be the same type of article of footwear as the article of footwear 302, and thus have the same footwear profile 322 as the article of footwear 302, or may be a different type of article of footwear and have a different footwear profile 322". The mobile device 308 may communicate with both of the first and second articles of footwear 302, 324 and the user may selectively control the motorized lacing system of each of the first and second articles of footwear 302, 324. It is to be understood that the same principle may be applied to an authorized secondary user described above, and may be applied to three or more different articles of footwear, e.g., all members of a team.

Figure 4:
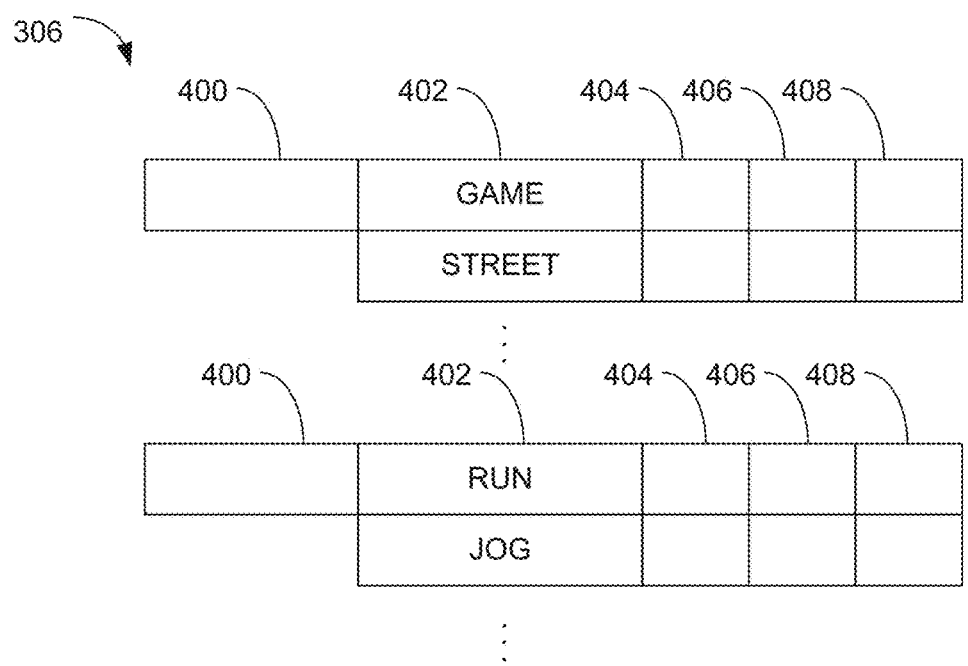
FIG. 4 is a block diagram representation of a user profile, in an example embodiment.

FIG. 4 is a block diagram representation of a user profile 306, in an example embodiment. The user profile 306 includes records 400 for multiple articles of footwear 302, with one record 400 corresponding to one pair of footwear 302. In various examples, one record 400 corresponds to any pair of footwear 302 of the same type or style such that the settings for one article of footwear 302 of the type or style may be expected to translate to or otherwise be immediately useful for another article of footwear 302 of the same style without modification. As such, a single record 400 may be applicable to may individual pairs of footwear 302, provided the pairs of footwear 302 are all sufficiently the same that the parameters and configurations specified in the record 400 may be applied to any footwear 302 of the same type.

Alternatively, each record 400 corresponds to a single pair of footwear 302. In such an example, the pair of footwear 302 may be identified with a unique identifier, e.g., via a nearfield communication (NFC) tag or a visible serial number or barcode, that may be associated with the record 400 and accessed to determine the identity of the article of footwear 302. Alternatively, the user may assign an identifier for the article of footwear 302 manually and then manually select the record 400 that is to be accessed. As such, the user profile 306 may be or function as a database that that stores multiple records 400.

Each record 400 includes an identifier field 402 to identify either the type for the article of footwear 302 or a unique identifier of the footwear 302 itself, as disclosed above. Each record 400 further includes a configuration label 402, and each configuration label 402 includes a left setting field 404, a right setting field 406. Each record further includes a calibration field 408, which will be described in detail herein. Each record 400 may be expanded to include multiple configuration labels 402 and associated setting fields 404, 406. In various examples, a given configuration label 402 may include more than just two setting fields 404, 406 dependent on the number of adaptive components of the article of footwear 302. Thus, for instance, if the article of footwear 302 included both the motorized lacing system 100 and a cushioning adapter then each configuration label 402 may link to the setting fields 404, 406 for the motorized lacing system 100, as well as left and right setting fields for the cushioning adapter.

Each configuration label 402 serves to identify a configuration that would be identifiable to and meaningful for the user. Thus, for instance, a configuration label may be "GAME", "WARMUP", "STREET", "RUN", "JOG", and so forth. Each configuration label 402 may be pre-set and/or manually selected, entered, or modified by user. The user may optionally add or remove configuration labels 402 and their associate setting fields 404, 406.

Each setting field 404, 406 includes information that, when transmitted to the processor circuit 204 of an associated left or right article of footwear 302, allows the processor circuit 204 to configure the motorized lacing system 100 to produce an expected tension on the lace. The information that may allow the processor circuit 204 to do so may depend on the specific implementation of the motorized lacing system 100. For instance, if a motorized lacing system 100 includes a strain gauge on the lace, then the information in the setting fields 404, 406 may correspond to a desired strain be sensed by the strain gauge. In the case of the motorized lacing system 100, the encoder 210 establishes a specific rotational position of the spool 220 and, as a consequence, an amount of lace which is unwound from the spool 220. The amount of lace unwound from the spool 220 directly corresponds to the amount of tension on the lace. Thus, in such an example, the information in the setting fields 404, 406 corresponds to an encoder setting that corresponds to the desired amount of lace wound on the spool 220.

FIGS. 5A-5E illustrate the user interface 310 displaying an app to pair the mobile device 308 with the articles of footwear 302, in an example embodiment. While a login screen is not depicted, the app may start by presenting the user with a login screen for an identifier for the user profile 306 and a password. The processor 312 may utilize the login information to verify the identity of the user (or other authorized secondary user) and then access the associated user profile 306 on one or both of the local electronic data storage 314 and the remote electronic data storage 318. If, as described above, the processor 312 determines that the user profile 306 as stored on the remote electronic data storage 318 is the most up-to-date user profile 306 available, the processor 312 may optionally download the user profile 306 to the local electronic data storage 314, or may continue to access the user profile 306 on the remote electronic data storage 318. Alternatively, if the processor 312 determines that the user profile 306 on the local data storage 314 is the most up-to-date, the processor 312 may transmit the user profile 306 to be stored on the remote electronic data storage 318.

Figure 5A:
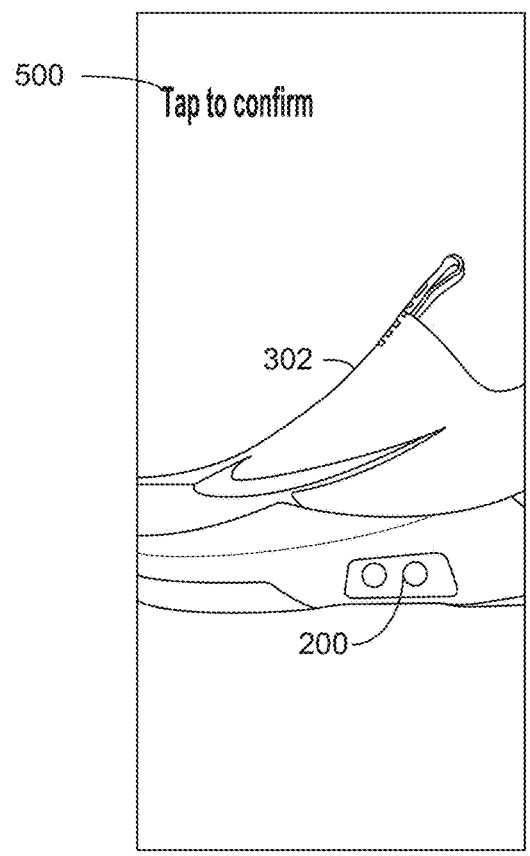
FIGS. 5A-5E illustrate the user interface displaying an app to pair the mobile device with the articles of footwear, in an example embodiment.
Figure 5B:
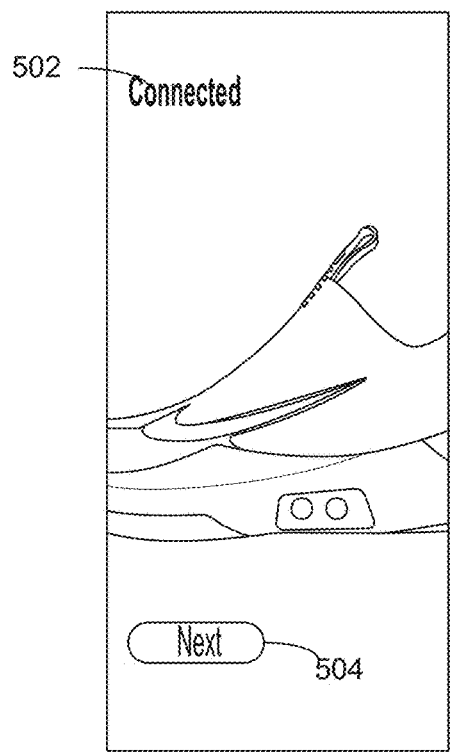
Figure 5C:
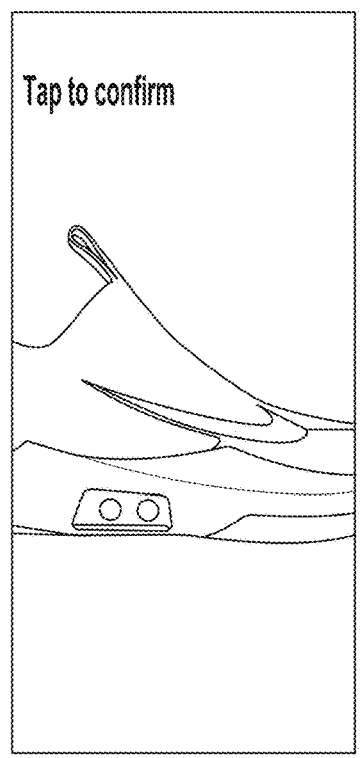
Figure 5D:
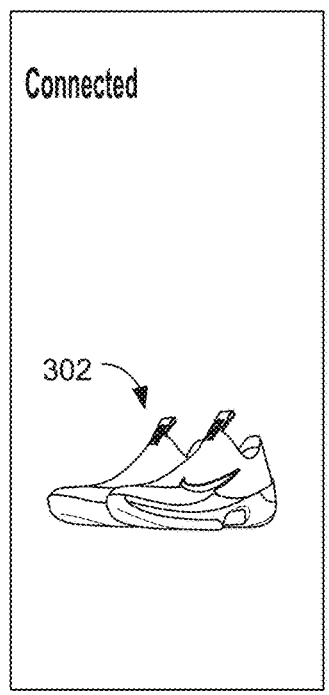
Figure 5E:
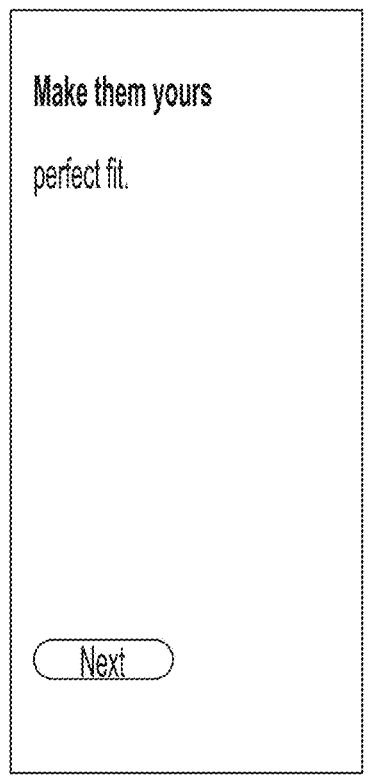

FIGS. 5A-5E illustrate how the app connects with the articles of footwear 302. Text 500 prompts the user to press one of the buttons 200 on the left article of footwear 302 in FIG. 5A. Text 502 on FIG. 5B confirms that the left article of footwear 302 has been identified and provides a soft button 504 to proceed to FIG. 5C and repeat the process for the right article of footwear 302. The pressing of each button 200 causes the processor circuit 204 to cause the coil 208 to transmit a wireless signal that may be detected by the wireless transceiver 316, the output of which may be interpreted by the processor 312 as being the button press that was prompted. FIG. 5D displays a confirmation that both articles of footwear 302 have been identified, following which, FIG. 5E prompts the user to proceed to select and adjust configurations for the motorized lacing system 100.

Figure 6A:
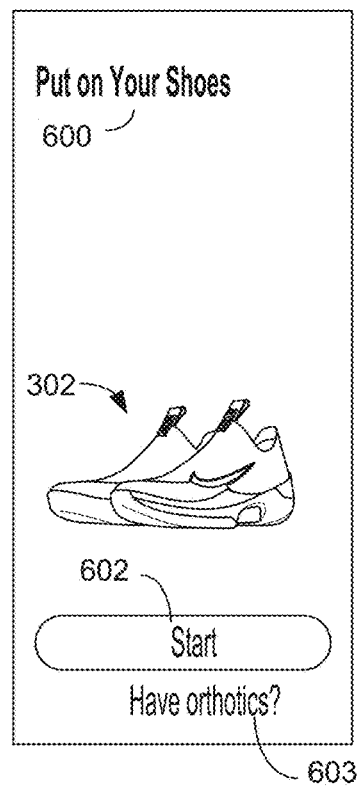
FIGS. 6A and 6B illustrate a calibration process that may be implemented for a given pair of footwear, in an example embodiment.
Figure 6B:
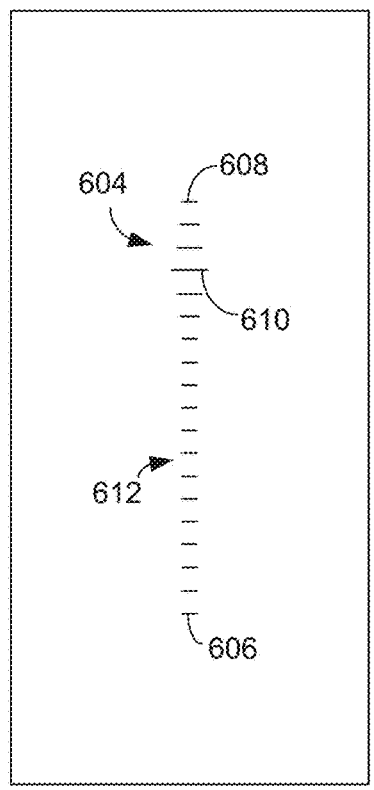

FIGS. 6A and 6B illustrate a calibration process that may be implemented for a given pair of footwear 302, in an example embodiment. The calibration process may be conducted if a record 400 for the articles of footwear 302 did not previously exist, e.g., if the user has not previously worn or manipulated the articles of footwear 302. Alternatively, the calibration process may be conducted based on a periodic prompting to ensure that the pair of footwear 302 remains calibrated, or based on a user selection via the user interface 310 to run the calibration process.

FIG. 6A illustrates a prompting screen, in which text 600 alerts the user that the articles of footwear 302 are going to be calibrated and provides a soft button 602 to begin the calibration. An orthotics soft button 603 provides for the insertion of one or more orthotics into the articles of footwear 302 before commencing the calibration. FIG. 6B provides a graphic illustration of the calibration process and the outcome. In particular, the graphic illustration includes a vertical scale 604 that ranges from a loose setting 606 to a maximally tight setting 608. The maximally tight setting corresponds to the maximum amount of tension that the motorized lacing system 100 can impart on the lace. As illustrate, one bar 610 on the scale 604 is larger than the rest of the bars 612, signifying a current degree of tension on the laces. The largest bar 610 may travel up the scale 604 until a calibration condition is met, whereupon the largest bar 610 may stop at a location corresponding to the calibrated maximum tension on the laces.

In an example, the motorized lacing system 100 determines the point of maximum tension on the lace by measuring a current induced through the motor 216. In particular, the harder the motor 216 operates to turn the spool 220, the greater the current the motor 216 draws from the battery 206. See, e.g., U.S. Pat. No. 9,365,387, "Motorized Tensioning System With Sensors", filed Aug. 30, 2013, and U.S. Application Publication No. 2016/0345681, Automated Tensioning System for an Article of Footwear", filed Dec. 1, 2015, both of which are incorporated by reference in their entirety. In an example, the motorized lacing system 100 measures the current that is being drawn by the motor 216. Upon reaching a predetermined maximum current, the state of the encoder 210 is noted. In an example, the predetermined maximum current is four Amperes. The state of the encoder 210 is then stored in the calibration field 408 and utilized by the app as the maximum point at which the encoder 210 may in future turn to before the motor 216 is disabled.

The calibration process may further be based, at least in part, on external information regarding the properties of the foot or feet of the user. For instance, the processor 312 may access, e.g., at the remote electronic data storage 318, information previously obtained about the foot or feet of the user. For instance, if the user has previously created a 3D scan of their foot (as disclosed in U.S. Pat. No. 10,062,097, "Three-Dimensional Body Scanning and Apparel Recommendation", filed May 31, 2017, which is incorporated by reference herein in its entirety), then the processor 314 may cross reference the information of the 3D scan against the associated footwear profile 322 to anticipate where the maximum may be or change the maximum. Thus, for instance, if the user has a relatively wide foot and the usual maximum tightness would be expected to be overly uncomfortable to the user, the processor 314 may change the maximum allowable tightness. Thus, for instance, if a comparison between the 3D scan of the user's foot and the footwear profile 322 indicates significant hotspots at a tightness corresponding to the usual four Amperes, the processor 314 may set the maximum at a motor current of three Amperes.

As will be illustrated herein, additional uses of the scale 604 to illustrate the tension on the lace and the general tightness of each article of footwear 302 may be expanded so that the maximum is at the top 608 of the scale 604 reflects the calibrated maximum. As such, a user would not be presented with the opportunity or option to increase the tightness higher than the calibrated maximum. However, in various examples the user may be presented with the option to remove the calibrated maximum.

Figure 7A:
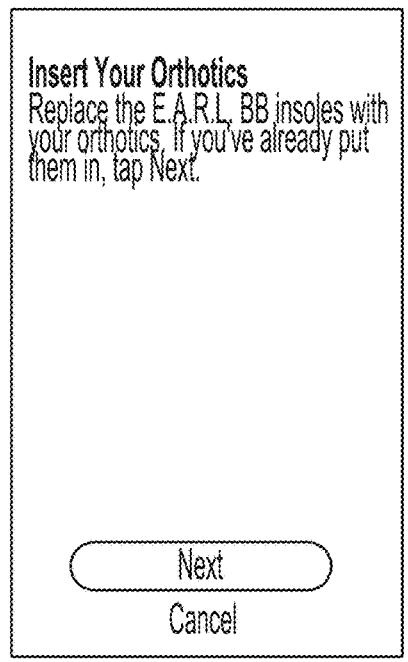
FIGS. 7A-7C illustrate conducting the calibration process with the addition of one or more orthotic inserts in the articles of footwear, in an example embodiment.
Figure 7B:
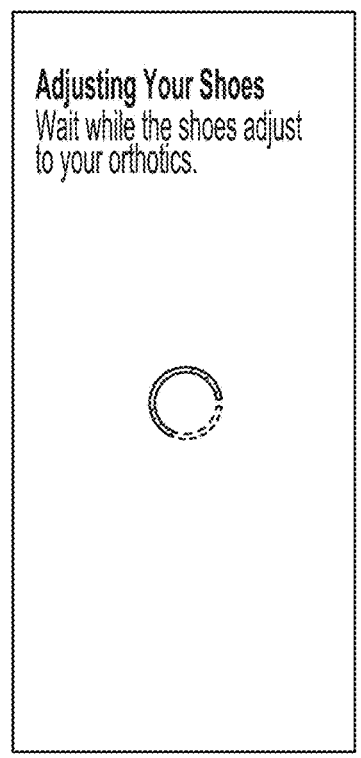
Figure 7C:
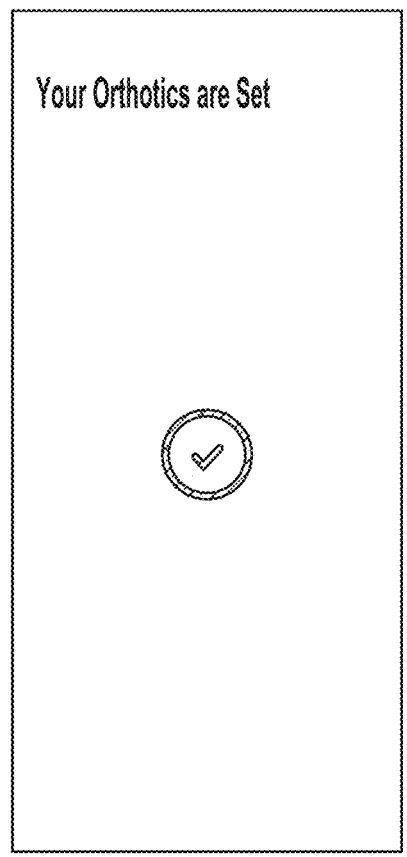

FIGS. 7A-7C illustrate conducting the calibration process with the addition of one or more orthotic inserts in the articles of footwear 302, in an example embodiment. If the user pressed the orthotics soft button 603 on the display in FIG. 6A, the app may proceed through the screens of FIGS. 7A-7C before proceeding to conducting the calibration illustrated in FIG. 6B.

In FIG. 7A the user is prompted to insert the orthotics into the articles of footwear 302. In FIG. 7B, the motorized lacing system 100 conducts a pre-calibration adjustment to determine an impact of the orthotics on various functions of the motorized lacing system 100. For instance, the foot presence sensor 202 may be recalibrated or otherwise put into a different, preset state. Once the orthotics pre-calibration is completed, the display in FIG. 7C is displayed and the app proceeds to conduct the full calibration.

FIGS. 8A-8E illustrate selecting and adjusting configurations for the articles of footwear 302, in an example embodiment. The principles disclosed here are related to changing or setting in the first instance a particular configuration. However, it is to be recognized and understood that the manual manipulation of the tightness of the laces may be performed without respect to any particular configuration.

Figure 8A:
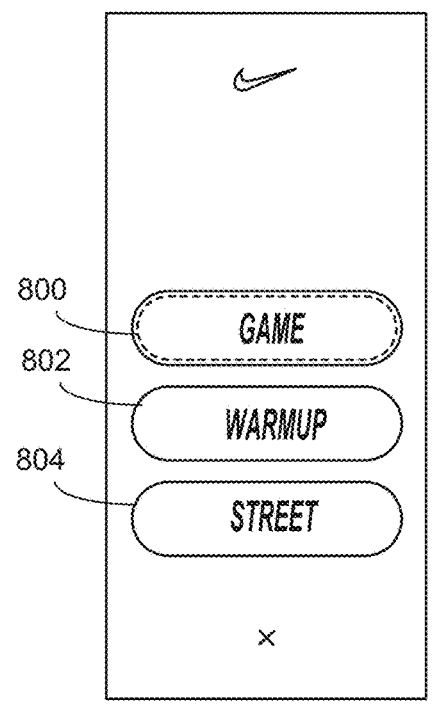
FIGS. 8A-8E illustrate selecting and adjusting configurations for the articles of footwear, in an example embodiment.

FIG. 8A is a user interface screen that allows a user to select one of three pre-set configuration soft buttons 800, 802, 804, each corresponding to a specific configuration. Each configuration corresponds to one record 400, with the name of each configuration being stored in a respective configuration label 402.

Figure 8B:
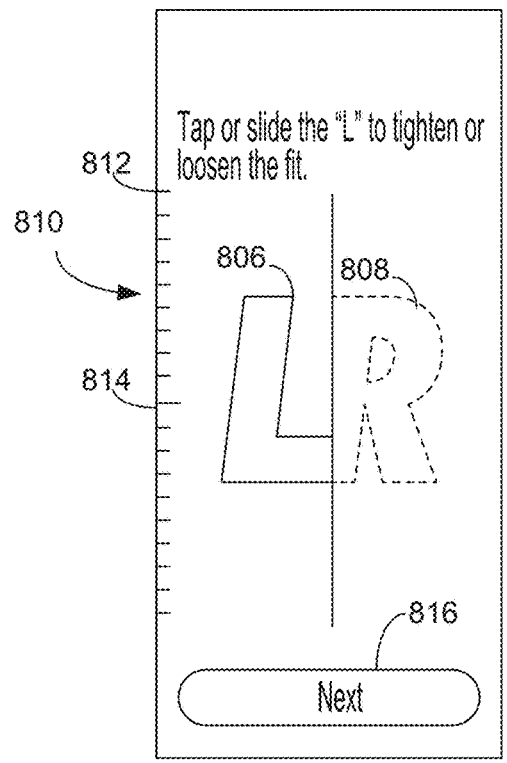

FIG. 8B is a user interface screen that is displayed upon the user selecting one of the configuration soft buttons 800, 802, 804, e.g., the GAME soft button 800. The user interface screen includes a left shoe icon 806, a right shoe icon 808, and a scale 810. In the illustrated example, the left shoe icon 806 is enabled while the right shoe icon 808 is disabled. The left shoe icon 806 may be slid up and down, corresponding to different locations on the scale 810. As the left shoe icon 806 is slid up and down, the motorized lacing system 100 increases or decrease the tightness on the lace of the left article of footwear 302 accordingly and proportionately. It is noted and emphasized that the scale 810 is the scale as calibrated, and that, in the example implementation provided herein, the top 812 of the scale corresponds to the tightness that is achievable at the maximum allowed motor current, e.g., four Amperes, and not the maximum tightness that the motorized lacing system 100 could possibly achieve with no artificially-calibrated limit. It is also noted that the scale 810 includes a larger dash 814 corresponding to the actual level of tightness of the left shoe icon 806. Upon setting the left shoe icon 806 to the desired tightness the user may select the next soft button 816 to move to the next screen. If the user wishes to return to an earlier screen, the user may select the return icon 818.

Figure 8C:
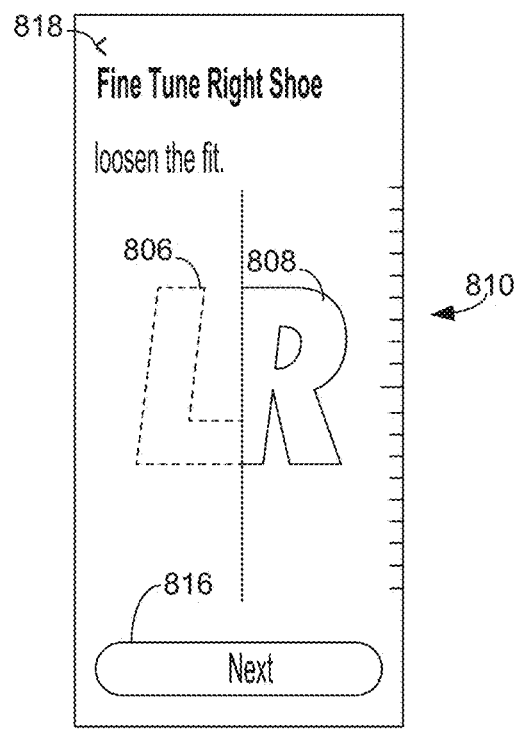

FIG. 8C is a user interface screen that is displayed upon the user selecting the NEXT soft button 816 in FIG. 8B. Now, the left shoe icon 806 is disabled and the right shoe icon 808 is enabled to be slid up and down to adjust the rightness of the right article of footwear 302 accordingly and proportionately. It is noted that the scale 810 has moved to the right side of the screen, in contrast to the scale 810 on FIG. 8B. Upon moving the right shoe icon 808 to the desired level, the user may select the next soft button 816. The user may select the return icon 818 to return to an earlier screen.

Figure 8D:
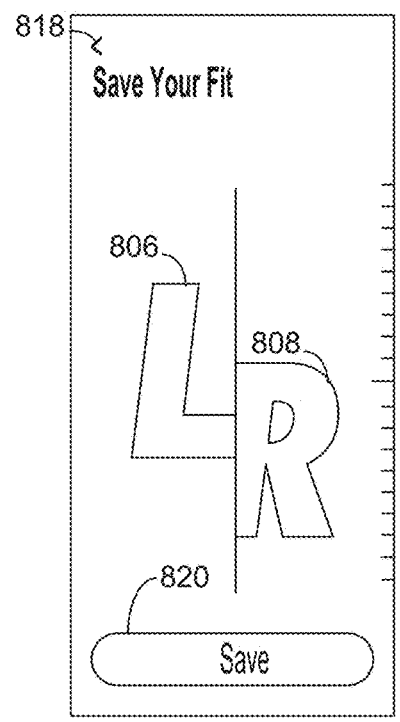

FIG. 8D is a user interface screen that allows the user to review their tension levels as illustrated by the left and right shoe icons 806, 808. In the illustrated example, both of the icons 806, 808 may be enabled for changes. Alternatively, both of the icons 806, 808 may be disabled. In such an example, if the user wishes to make any changes the user may select the return icon 818 to return to an appropriate earlier screen. If the user is satisfied with the tension on each article of footwear 302 the user may select the save soft button 820.

Figure 8E:
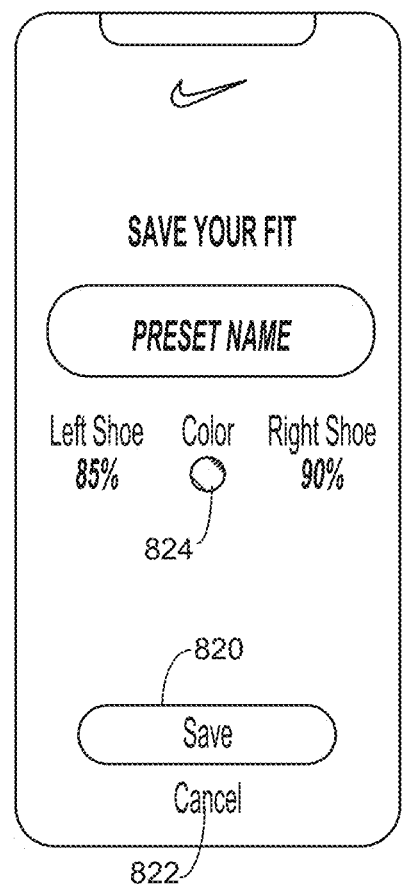

FIG. 8E is a user interface screen that allows the user to change the name of the configuration if desired. The user interface screen additionally shows a numerical value of the percentage degree of tightness of each of the articles of footwear 302. If the user presses the cancel soft button 822 the settings are not saved to the appropriate record 400. If the user presses the save soft button 820 then the setting for the left article of footwear 302 is saved to the left setting field 404 and the setting for the right article of footwear 302 is saved to the right setting field 406. The settings saved in the left and right setting fields 404, 406 may be translated as appropriate, e.g., to an encoder setting as described in detail above.

The user interface screen further includes a color icon 824 that allows a background color of the app screen to be changed. In the illustrated example, the color icon 824 allows the user to select a specific color to associate with the configuration at issue. In such an example, the color may be saved in the record as being associated with the configuration, and any time the configuration is selected by the user on the app the background color may change accordingly. It is to be recognized and understood that the record 400 may include a field to save the assigned color accordingly. It is also to be recognized that the use of the color icon 824 may apply not just to a particular configuration but rather to a record 400 in general, e.g., each individual pair of footwear 302 has their own color, or each individual article of footwear 302 has its own color, e.g., when the user interface screen of FIG. 8B is displayed and the left article of footwear 302 is being adjusted the background color is red and when the user interface screen of FIG. 8C is being displayed and the right article of footwear 302 is being adjusted the background color is blue, and so forth.

It is to be recognized and understood that the app as illustrated in FIGS. 8A-8E are not the only mechanism by which the motorized lacing system 100 may be manipulated. In particular, as has been noted herein, the buttons 200 may be pushed to selective increase and decrease the tension on the laces. When the buttons 200 are utilized, the position of the left and right shoe icons 806, 808 may be adjust on the app to reflect the actual tension on the laces. Further, alternative mechanisms for adjust the tension on the laces may be implemented.

For instance, gestures may be utilized, as disclosed in U.S. Patent Application Publication No. 2016/0262485, "Motorized Shoe With Gesture Control", filed Mar. 15, 2016, which is incorporated herein by reference in its entirety. In such an example, gestures may be assigned, e.g., to individual configurations, and the performance of the gesture may cause the motorized lacing system 100 to implement the predetermined configuration. Thus, for instance, a player in a basketball game may have their articles of footwear 302 in the WARMUP configuration and then, as the game is about to start, perform a "toe tap" gesture to cause their articles of footwear 302 to go into the GAME mode. The app may additionally allow gestures to be customized according to user preference. Gestures for various configurations may additionally be shared between and among user profiles 306, e.g., if one user would like to make gestures they use available to a different user.

It is to be further recognized and understood that the user profile 306 may incorporate capacity to store additional information related to the user. Thus, for instance, in addition to personal information about the user such as name and so forth, the user profile 306 may additionally store sensor data obtained from the motorized lacing system 100. Thus, data from the foot presence sensor 202, magnetometer 222, environment sensor 224, motion sensor 212, and so forth may be stored in the user profile 306 and potentially used to identify performance characteristics of the user.

Figure 9:
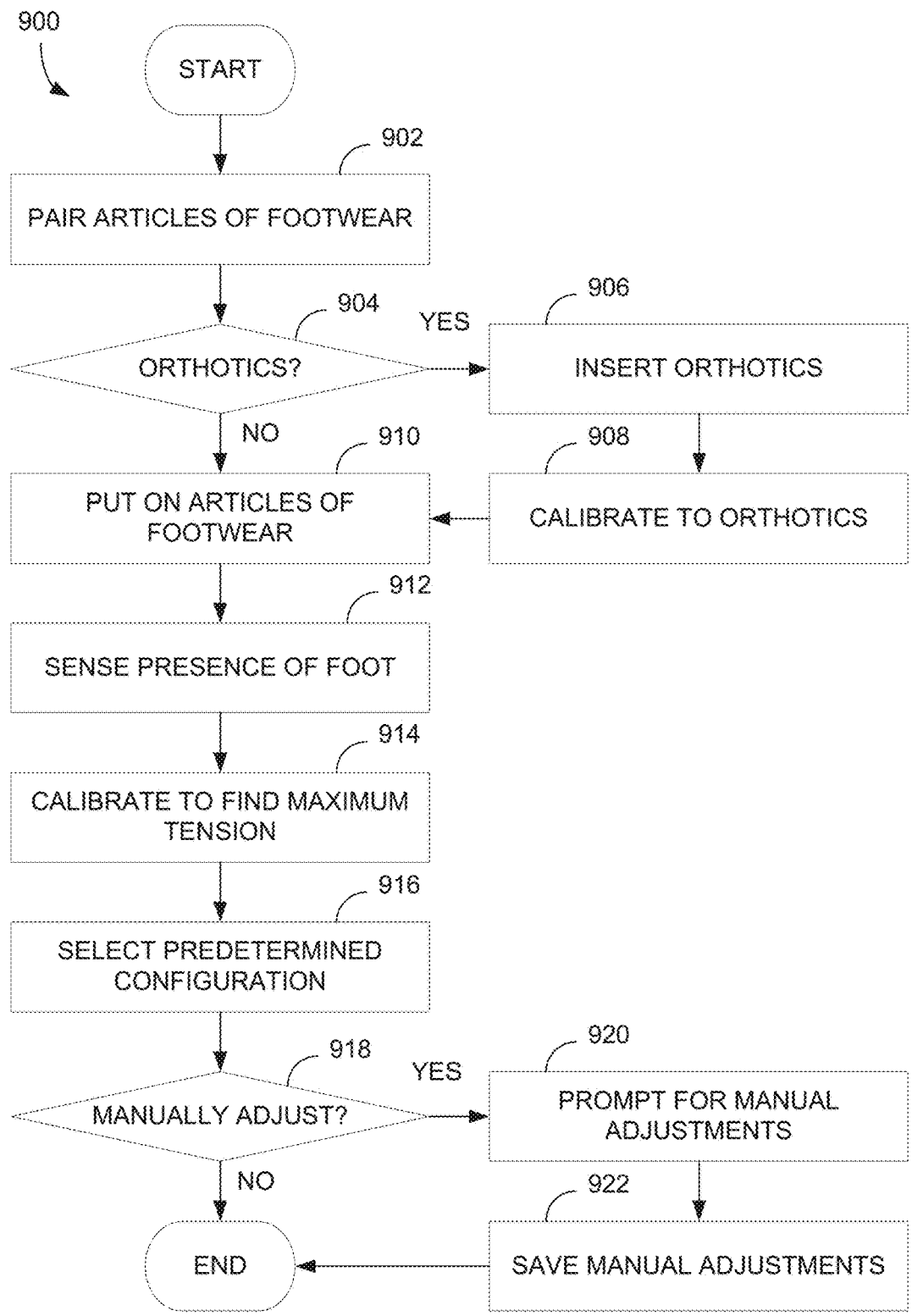
FIG. 9 is a flowchart for calibrating articles of footwear and setting a predetermined configuration, in an example embodiment.

FIG. 9 is a flowchart 900 for calibrating articles of footwear 302 and setting a predetermined configuration, in an example embodiment. The flowchart 900 references the app illustrated in FIGS. 5-8 herein, but may be utilized with respect to any suitable user interface.

At 902, the app prompts the user to commence the process and pair the articles of footwear 302, as illustrated in FIGS. 5A-5E.

At 904, the app prompts the user whether or not the user if wearing orthotics, as illustrated in FIG. 6A. If the user is using orthotics, the flowchart 900 proceeds to 906. If the user is not using orthotics, the flowchart 900 proceeds to 910.

At 906, the user is prompted to insert the orthotics, as illustrated in FIG. 7A.

At 908, the user is prompted to wait while the motorized lacing system are calibrated to the orthotics, as illustrated in FIGS. 7B and 7C.

At 910, the user is prompted to put the articles of footwear on, as illustrated in FIG. 6A.

At 912, the motorized lacing systems 100 sense the presence of the foot using the foot presence sensor 202 and operates the motor to fully loosened. This process is not necessarily illustrated or otherwise presented to the user on the app.

At 914, the articles of footwear 302 are calibrated to the user to find the maximum tension, as illustrated in FIG. 6B. The result is saved in the calibration field 410.

At 916, the user is prompted to select a preset, predetermined configuration, as illustrated in FIG. 8A.

At 918, the user is optionally prompted for if the user would like to manually adjust the tension on the laces.

At 920, if the user chooses to adjust the manually adjust the tension on the laces, the user is prompted to do so, as illustrated in FIGS. 8B and 8C.

At 922, the user is prompted to save the adjustments to the configuration by updating the left and right shoe fields 406, 408 in the record 400, as illustrated in FIGS. 8D and 8E.

EXAMPLES

In Example 1, a system includes an article of footwear and a remote system. The article of footwear includes a wireless transceiver, a processor circuit operatively coupled to the wireless transceiver, and an adaptive component, operatively coupled to the processor circuit, configured to be adjusted to one of a plurality of configurations based on a command received from the processor circuit. The remote system includes an electronic data storage, configured to store a user profile including the plurality of configurations, a user interface, a wireless transceiver configured to communicatively couple to the wireless transceiver of the article of footwear, and a processor, operatively coupled to the user interface and the wireless transceiver, the processor configured to prompt, on the user interface, the user to put on the article of footwear, receive, via the wireless transceiver, a signal from the article of footwear indicating that the article of footwear has been placed on the foot of a wearer, command, via the wireless transceiver, the adaptive component to perform a calibration to identify a maximum property of the adaptive component, receive, via the wireless transceiver, a signal from the article of footwear indicating what the maximum property is, recalibrating the plurality of configurations to prevent any of the plurality of configurations from exceeding the maximum property, and transmitting, via the wireless transceiver, one of the plurality of configurations as recalibrated, wherein, upon receiving the one of the plurality of configurations, the processor circuit causes the adaptive component to be configured according to the one of the plurality of configurations.

In Example 2, the system of Example 1 optionally further includes that the adaptive component comprises a motor and wherein the calibration includes measuring a current through the motor.

In Example 3, the system of either one or more of Examples 1 and 2 optionally further includes that the motor is operated until the current through the motor meets a predetermined maximum current.

In Example 4, the system of either one or more of Examples 1-3 optionally further includes that the adaptive component further includes an encoder, and wherein the processor circuit is configured to transmit, as the signal indicating the maximum property, a setting of the encoder that corresponds to when the motor meets the predetermined maximum current.

In Example 5, the system of either one or more of Examples 1-4 optionally further includes that the plurality of configurations are part of the user profile stored in the electronic data storage, wherein the user profile further comprises a database to store multiple records, each record comprising one plurality of configurations associated with a particular article of footwear.

In Example 6, the system of either one or more of Examples 1-5 optionally further includes that the adaptive component is a motorized lacing system, and wherein each of the plurality of configurations describes a degree of tension on a lace induced by the motorized lacing system.

In Example 7, the system of either one or more of Examples 1-6 optionally further includes that the motorized lacing system comprises a motor, a spool, and an encoder configured to determine a rotational position of the spool, and wherein the each of the plurality of configurations describes an encoder setting corresponding to a desired degree of tension on the lace.

In Example 8, the system of either one or more of Examples 1-7 optionally further includes that the processor is further configured to prompt a user, via the user interface, to manually adjust the degree of tension on the lace based on a user input from the user and update the one of the plurality of configurations based on the degree of tension as manually adjusted.

In Example 9, the system of either one or more of Examples 1-8 optionally further includes that the remote system comprises a mobile device, and wherein the user interface, the wireless transceiver, the electronic data storage, and the processor are components of the mobile device.

In Example 10, the system of either one or more of Examples 1-9 optionally further includes that the remote system further comprises a remote electronic data storage accessible via a network connection by the mobile device, wherein the remote electronic data storage is configured to store the user profile including the plurality of configurations, and wherein the processor is further configured to download the plurality of configurations from the remote electronic data storage.

in Example 11, a system includes an article of footwear and a remote system. The article of footwear includes a wireless transceiver, a processor circuit operatively coupled to the wireless transceiver, and an adaptive component, operatively coupled to the processor circuit, configured to be adjusted to one of a plurality of configurations based on a command received from the processor circuit. The remote system includes an electronic data storage, configured to store a user profile including the plurality of configurations, a user interface, a wireless transceiver configured to communicatively couple to the wireless transceiver of the article of footwear, and a processor, operatively coupled to the user interface and the wireless transceiver, the processor configured to prompt, on the user interface, the user to put on the article of footwear, receive, via the wireless transceiver, a signal from the article of footwear indicating that the article of footwear has been placed on the foot of a wearer, access, in the electronic data storage, one of the plurality of configurations based on a user selection received via the user interface, and transmit, via the wireless transceiver, the one of the plurality of configurations as selected, wherein, upon receiving the one of the plurality of configurations, the processor circuit causes the adaptive component to be configured according to the one of the plurality of configurations.

In Example 12, the system of Example 11 optionally further includes that the plurality of configurations are part of the user profile stored in the electronic data storage, wherein the user profile further comprises a database to store multiple records, each record comprising one plurality of configurations associated with a particular article of footwear.

In Example 13, the system of any one or more of Examples 11 and 12 optionally further includes that the adaptive component is a motorized lacing system, and wherein each of the plurality of configurations describes a degree of tension on a lace induced by the motorized lacing system.

In Example 14, the system of any one or more of Examples 11-13 optionally further includes that the motorized lacing system comprises a motor, a spool, and an encoder configured to determine a rotational position of the spool, and wherein the each of the plurality of configurations describes an encoder setting corresponding to a desired degree of tension on the lace.

In Example 15, the system of any one or more of Examples 11-14 optionally further includes that the processor is further configured to prompt a user, via the user interface, to manually adjust the degree of tension on the lace based on a user input from the user and update the one of the plurality of configurations based on the degree of tension as manually adjusted.

In Example 16, a computer readable medium includes instructions which, when implemented by a processor, cause the processor to perform operations comprising prompt, on a user interface of a remote system, a user to put on an article of footwear, the article of footwear comprising a wireless transceiver, a processor circuit operatively coupled to the wireless transceiver, and an adaptive component, operatively coupled to the processor circuit, configured to be adjusted to one of a plurality of configurations based on a command received from the processor circuit, receive, via a wireless transmitter of the remote system, a signal from the article of footwear indicating that the article of footwear has been placed on the foot of a wearer, command, via the wireless transceiver, the adaptive component to perform a calibration to identify a maximum property of the adaptive component, receive, via the wireless transceiver, a signal from the article of footwear indicating what the maximum property is, recalibrate the plurality of configurations to prevent any of the plurality of configurations from exceeding the maximum property, and transmitting, via the wireless transceiver, one of the plurality of configurations as recalibrated, wherein, upon receiving the one of the plurality of configurations, the processor circuit causes the adaptive component to be configured according to the one of the plurality of configurations.

In Example 17, the system of Example 16 optionally further includes that the adaptive component comprises a motor and wherein the calibration includes measuring a current through the motor.

In Example 18, the system of either one or more of Examples 16 and 17 optionally further includes that the motor is operated until the current through the motor meets a predetermined maximum current.

In Example 19, the system of either one or more of Examples 16-18 optionally further includes that the adaptive component further includes an encoder, and wherein the processor circuit is configured to transmit, as the signal indicating the maximum property, a setting of the encoder that corresponds to when the motor meets the predetermined maximum current.

In Example 20, the system of either one or more of Examples 16-19 optionally further includes that the plurality of configurations are part of the user profile stored in the electronic data storage, wherein the user profile further comprises a database to store multiple records, each record comprising one plurality of configurations associated with a particular article of footwear.

In Example 21, the system of either one or more of Examples 16-20 optionally further includes that the adaptive component is a motorized lacing system, and wherein each of the plurality of configurations describes a degree of tension on a lace induced by the motorized lacing system.

In Example 22, the system of either one or more of Examples 16-21 optionally further includes that the motorized lacing system comprises a motor, a spool, and an encoder configured to determine a rotational position of the spool, and wherein the each of the plurality of configurations describes an encoder setting corresponding to a desired degree of tension on the lace.

In Example 23, the system of either one or more of Examples 16-22 optionally further includes that the processor is further configured to prompt a user, via the user interface, to manually adjust the degree of tension on the lace based on a user input from the user and update the one of the plurality of configurations based on the degree of tension as manually adjusted.

In Example 24, the system of either one or more of Examples 16-23 optionally further includes that the remote system comprises a mobile device, and wherein the user interface, the wireless transceiver, the electronic data storage, and the processor are components of the mobile device.

in Example 25, the system of either one or more of Examples 16-24 optionally further includes that the remote system further comprises a remote electronic data storage accessible via a network connection by the mobile device, wherein the remote electronic data storage is configured to store the user profile including the plurality of configurations, and wherein the processor is further configured to download the plurality of configurations from the remote electronic data storage.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field programmable gate array (FPGA) or an ASIC. A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, a processor being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an application program interface (API)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

BRIEF SUMMARY OF THE INVENTION

A system includes an article of footwear and a remote system. The article of footwear includes an adaptive configured to be adjusted to one of a plurality of configurations based on a command received from a processor circuit. The remote system includes an electronic data storage, configured to store a user profile including the plurality of configurations, and a processor configured to prompt, on a user interface, a user to put on the article of footwear, receive, via a wireless transceiver, a signal from the article of footwear indicating that the article of footwear has been placed on the foot of a wearer, access, one of the plurality of configurations based on a user selection, and transmit the one of the plurality of configurations as selected. The processor circuit causes the adaptive component to be configured according to the one of the plurality of configurations.

What is claimed is:

1. A system, comprising:
    an article of footwear, comprising:
        a wireless transceiver;
        a processor circuit operatively coupled to the wireless transceiver; and
        an adaptive component, operatively coupled to the processor circuit, configured to be adjusted to one of a plurality of configurations based on a command received from the processor circuit;
    a remote system, comprising:
        an electronic data storage, configured to store a user profile including the plurality of configurations;
        a user interface;
        a wireless transceiver configured to communicatively couple to the wireless transceiver of the article of footwear; and
        a processor, operatively coupled to the user interface and the wireless transceiver of the remote system, the processor configured to:
    prompt, on the user interface, a wearer to put on the article of footwear;
    receive, via the wireless transceiver of the remote system, a signal from the article of footwear indicating that the article of footwear has been placed on a foot of the wearer;
    command, based on receiving the signal, via the wireless transceiver of the remote system, the adaptive component to perform a calibration to identify a maximum property of the adaptive component;
    receive, via the wireless transceiver of the remote system, a signal from the article of footwear indicating what the maximum property is;
    calibrate the plurality of configurations to prevent any of the plurality of configurations from exceeding the maximum property; and
    transmit, via the wireless transceiver, one of the plurality of configurations as calibrated;
    wherein, upon receiving the one of the plurality of configurations, the processor circuit causes the adaptive component to be configured according to the one of the plurality of configurations.

2. The system of claim 1, wherein the adaptive component comprises a motor and wherein the calibration includes measuring a current through the motor.

3. The system of claim 2, wherein the motor is operated until the current through the motor meets a predetermined maximum current.

4. The system of claim 3, wherein the adaptive component further includes an encoder, and wherein the processor circuit is configured to transmit, as the signal indicating the maximum property, a setting of the encoder that corresponds to when the motor meets the predetermined maximum current.

5. The system of claim 1, wherein the plurality of configurations are part of the user profile stored in the electronic data storage, wherein the user profile further comprises a database to store multiple records, each record comprising one plurality of configurations associated with a particular article of footwear.

6. The system of claim 5, wherein the adaptive component is a motorized lacing system, and wherein each of the plurality of configurations describes a degree of tension on a lace induced by the motorized lacing system.

7. The system of claim 6, wherein the motorized lacing system comprises a motor, a spool, and an encoder configured to determine a rotational position of the spool, and wherein the each of the plurality of configurations describes an encoder setting corresponding to a desired degree of tension on the lace.

8. The system of claim 6, wherein the processor is further configured to:
prompt a user, via the user interface, to manually adjust the degree of tension on the lace based on a user input from the user; and
update the one of the plurality of configurations based on the degree of tension as manually adjusted.

9. The system of claim 1, wherein the remote system comprises a mobile device, and wherein the user interface, the wireless transceiver of the remote system, the electronic data storage, and the processor are components of the mobile device.

10. The system of claim 9, wherein the remote system further comprises a remote electronic data storage accessible via a network connection by the mobile device, wherein the remote electronic data storage is configured to store the user profile including the plurality of configurations, and wherein the processor is further configured to download the plurality of configurations from the remote electronic data storage.

11. A non-transitory computer readable medium comprising instructions which, when implemented by a processor, cause the processor to perform operations comprising:
prompt, on a user interface of a remote system, a wearer to put on an article of footwear, the article of footwear comprising a wireless transceiver, a processor circuit operatively coupled to the wireless transceiver of the article of footwear, and an adaptive component, operatively coupled to the processor circuit, configured to be adjusted to one of a plurality of configurations based on a command received from the processor circuit;
receive, via a wireless transceiver of the remote system, a signal from the article of footwear indicating that the article of footwear has been placed on a foot of the wearer;
command, based on receiving the signal, via the wireless transceiver of the remote system, the adaptive component to perform a calibration to identify a maximum property of the adaptive component;
receive, via the wireless transceiver of the remote system, a signal from the article of footwear indicating what the maximum property is;
calibrate the plurality of configurations to prevent any of the plurality of configurations from exceeding the maximum property; and
transmitting, via the wireless transceiver of the remote system, one of the plurality of configurations as calibrated;
wherein, upon receiving the one of the plurality of configurations, the processor circuit causes the adaptive component to be configured according to the one of the plurality of configurations.

12. The computer readable medium of claim 11, wherein the adaptive component comprises a motor and wherein the calibration includes measuring a current through the motor.

13. The computer readable medium of claim 12, wherein the motor is operated until the current through the motor meets a predetermined maximum current.

14. The computer readable medium of claim 13, wherein the adaptive component further includes an encoder, and wherein the processor circuit is configured to transmit, as the signal indicating the maximum property, a setting of the encoder that corresponds to when the motor meets the predetermined maximum current.

15. The computer readable medium of claim 11, wherein the plurality of configurations are part of the user profile stored in the electronic data storage, wherein the user profile further comprises a database to store multiple records, each record comprising one plurality of configurations associated with a particular article of footwear.

16. The computer readable medium of claim 15, wherein the adaptive component is a motorized lacing system, and wherein each of the plurality of configurations describes a degree of tension on a lace induced by the motorized lacing system.

17. The computer readable medium of claim 16, wherein the motorized lacing system comprises a motor, a spool, and an encoder configured to determine a rotational position of the spool, and wherein the each of the plurality of configurations describes an encoder setting corresponding to a desired degree of tension on the lace.

18. The computer readable medium of claim 16, wherein the instruction further cause the processor to perform operations comprising:
prompt a user, via the user interface, to manually adjust the degree of tension on the lace based on a user input from the user; and
update the one of the plurality of configurations based on the degree of tension as manually adjusted.

19. The computer readable medium of claim 11, wherein the remote system comprises a mobile device, and wherein the user interface, the wireless transceiver of the remote system, the electronic data storage, and the processor are components of the mobile device.

20. The computer readable medium of claim 19, wherein the remote system further comprises a remote electronic data storage accessible via a network connection by the mobile device, wherein the remote electronic data storage is configured to store the user profile including the plurality of configurations, and wherein the processor is further configured to download the plurality of configurations from the remote electronic data storage.

21. A processor-implemented method, comprising:
prompting, on a user interface of a remote system, a wearer to put on an article of footwear, the article of footwear comprising a wireless transceiver, a processor circuit operatively coupled to the wireless transceiver of the article of footwear, and an adaptive component, operatively coupled to the processor circuit, configured to be adjusted to one of a plurality of configurations based on a command received from the processor circuit;
receiving, via a wireless transceiver of the remote system, a signal from the article of footwear indicating that the article of footwear has been placed on a foot of the wearer;
commanding, based on receiving the signal, via the wireless transceiver of the remote system, the adaptive component to perform a calibration to identify a maximum property of the adaptive component;

receiving, via the wireless transceiver of the remote system, a signal from the article of footwear indicating what the maximum property is;

calibrating the plurality of configurations to prevent any of the plurality of configurations from exceeding the maximum property; and transmitting, via the wireless transceiver of the remote system, one of the plurality of configurations as calibrated;

upon receiving the one of the plurality of configurations, causing the adaptive component to be configured according to the one of the plurality of configurations.

22. The method of claim 21, wherein the adaptive component comprises a motor and wherein the calibration includes measuring a current through the motor.

23. The method of claim 22, wherein the motor is operated until the current through the motor meets a predetermined maximum current.

24. The method of claim 23, wherein the adaptive component further includes an encoder, and further comprising transmitting, as the signal indicating the maximum property, a setting of the encoder that corresponds to when the motor meets the predetermined maximum current.

25. The method of claim 21, wherein the plurality of configurations are part of the user profile stored in the electronic data storage, wherein the user profile further comprises a database to store multiple records, each record comprising one plurality of configurations associated with a particular article of footwear.

26. The method of claim 25, wherein the adaptive component is a motorized lacing system, and wherein each of the plurality of configurations describes a degree of tension on a lace induced by the motorized lacing system.

27. The method of claim 26, wherein the motorized lacing system comprises a motor, a spool, and an encoder configured to determine a rotational position of the spool, and wherein the each of the plurality of configurations describes an encoder setting corresponding to a desired degree of tension on the lace.

28. The method of claim 26, further comprising:

prompting a user, via the user interface, to manually adjust the degree of tension on the lace based on a user input from the user; and updating the one of the plurality of configurations based on the degree of tension as manually adjusted.

* * * * *